United States Patent [19]

Kurtz et al.

[11] Patent Number: 4,500,308
[45] Date of Patent: Feb. 19, 1985

[54] AUTOTRANSFUSION DEVICE WITH TWISTED COLLECTION BAG

[75] Inventors: Leonard D. Kurtz, Woodmere; Joseph LiCausi, Port Jefferson Station, both of N.Y.

[73] Assignee: BioResearch Inc., Farmingdale, N.Y.

[21] Appl. No.: 441,991

[22] Filed: Nov. 16, 1982

[51] Int. Cl.³ .............................................. A61M 1/03
[52] U.S. Cl. ...................................... 604/4; 222/104; 222/390; 604/135; 604/214
[58] Field of Search ............... 604/134, 135, 141, 204, 604/212, 214, 218, 224, 319–321, 4–6; 222/95, 104, 390

[56] References Cited

U.S. PATENT DOCUMENTS

| | | | |
|---|---|---|---|
| 1,959,365 | 5/1934 | Jeffreys | 222/104 |
| 2,699,167 | 1/1955 | Raiche | 604/134 |
| 2,950,717 | 8/1960 | Bouet | 604/214 |
| 3,048,171 | 8/1962 | Grau | 604/134 |
| 3,223,289 | 12/1965 | Bouet | 222/95 |
| 4,033,345 | 7/1977 | Sorensen et al. | 604/4 |
| 4,424,053 | 1/1984 | Kurtz et al. | 604/4 |

FOREIGN PATENT DOCUMENTS

| | | | |
|---|---|---|---|
| 1288915 | 2/1962 | France | 222/95 |
| 495856 | 2/1938 | United Kingdom | 222/104 |

*Primary Examiner*—Dalton L. Truluck
*Attorney, Agent, or Firm*—Larson and Taylor

[57] ABSTRACT

An autotransfusion device having a rigid cylindrical housing with an end wall, a movable piston located in the housing, and a deformable collection bag attached between the end wall and the piston is disclosed. When the piston is moved towards the end wall, collapsing the collection bag, the piston is rotated to twist the collection bag and prevent the collection bag from being seized between the housing wall and the piston. The autotransfusion device also includes an automatic air purge unit and an auxiliary air purge unit which is used when the automatic air purge unit malfunctions. In order to facilitate the filling of the collection bag to capacity, a length to diameter ratio of 1.1 is preferred.

14 Claims, 2 Drawing Figures

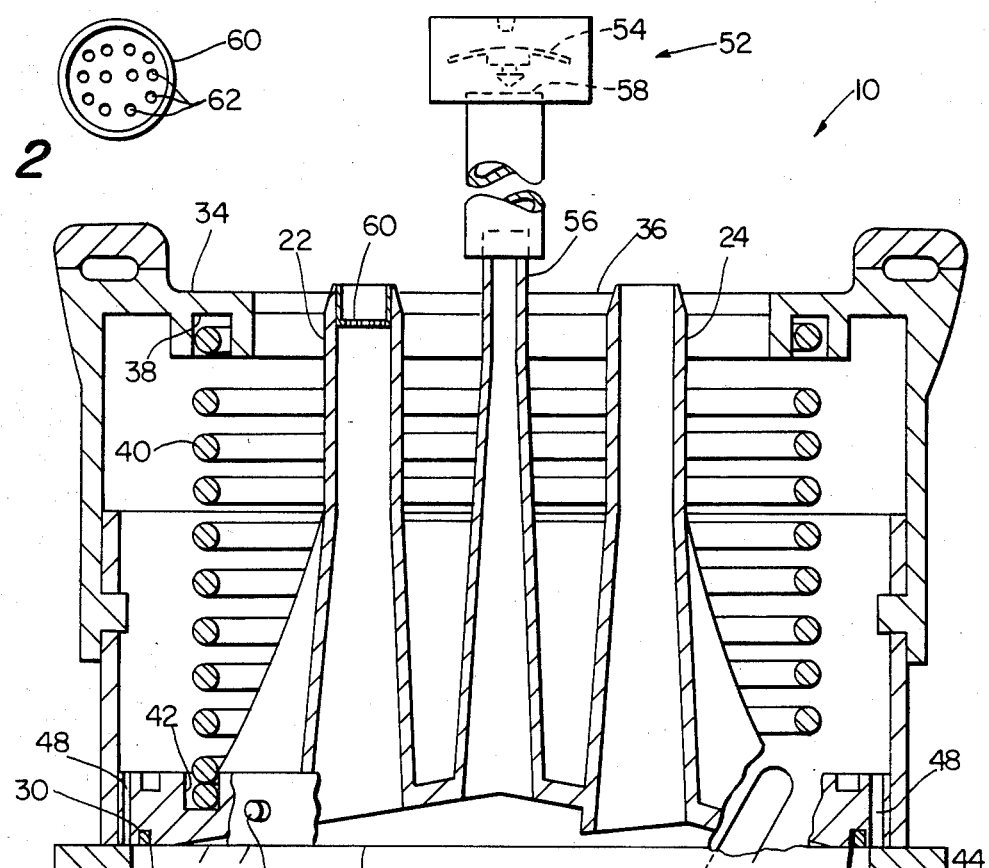
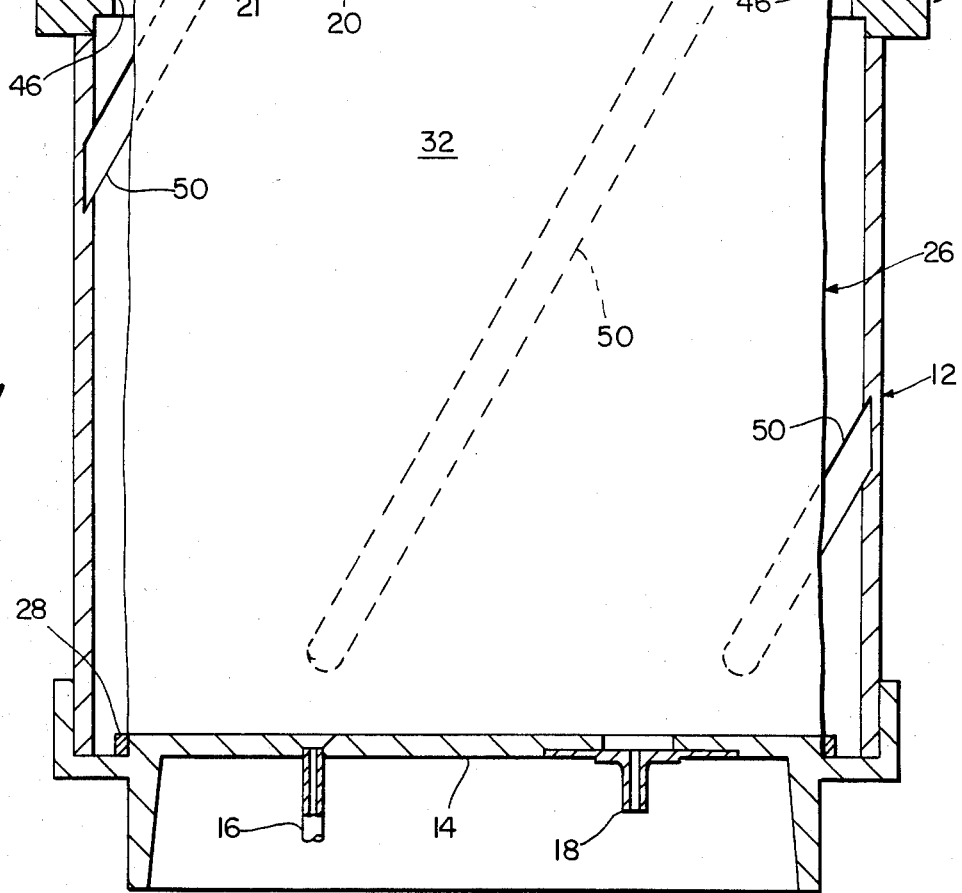
FIG. 2
FIG. 1

4,500,308

AUTOTRANSFUSION DEVICE WITH TWISTED COLLECTION BAG

FIELD OF THE INVENTION

This invention relates generally to an autotransfusion device and more particularly to the provision of a twisting action on the collection bag in the autotransfusion device to prevent seizing of the bag.

BACKGROUND OF THE INVENTION

During certain types of surgery, particularly in connection with chest cavity surgery, the patient frequently loses large amounts of blood. Ordinarily, the lost blood is aspired away and the patient is given a transfusion of donated blood to make up for the lost blood. An alternative arrangement is to provide an autotransfusion device which will collect the blood lost by the patient and transfuse this blood into the patient's circulatory system.

There are disclosed in the prior art various systems for autotransfusion. For example, in the U.S. Pat. No. 3,191,600 (Everett) an autotransfusion apparatus is disclosed which includes a vacuum source and a plurality of suction tips for immersion in pools of blood. The blood is collected in a collection chamber and is returned to the patient through a oneway valve. Another autotransfusion device is disclosed in U.S. Pat. No. 3,492,991 (Dyer) and includes a container equipped with a filter through which the blood is gravity fed back to the patient. In U.S. Pat. No. 3,993,067 (Schachet et al) an autotransfusion device is disclosed in which the blood is forced back into the patient by pressure in the collection chamber. Still another autotransfusion device is disclosed in U.S. Pat. No. 4,047,526 (Reynolds et al). This patent discloses a collection chamber in which blood is continuously aspirated. A blood bag with an outwardly urged spring is connected to the collection chamber to withdraw some of the blood therefrom. The blood collected in the blood bag is then later reintroduced into the patient. There has also been disclosed in the prior art a spring operated device which forces blood from a blood bag into the patient. Such a device is disclosed in U.S. Pat. No. 3,565,292 (Jinotti).

The applicants of the present invention have previously filed an application for a novel autotransfusion device which is efficient and simple to operate. This application is Ser. No. 290,666 and was filed on Aug. 5, 1981 now U.S. Pat. No. 4,424,053. Applicants have also filed a continuation-in-part application on Aug. 14, 1981, now U.S. Pat. No. 4,445,884 with an air purge unit for applicant's autotransfusion device. This air purge unit insures that all air within the collection chamber is automatically eliminated before the blood is reintroduced into the patient's circulatory system.

SUMMARY OF THE INVENTION

In accordance with the present invention, an autotransfusion device for collecting blood from a pool in a patient and for subsequently returning the collected blood to the circulatory system of the patient is disclosed. The autotransfusion device includes a cylindrical housing having an end wall and a side wall, and a moveable piston located in the housing. A generally cylindrical, deformable collection bag is also located in the housing with the peripheral ends attached to, respectively, the end wall and the piston so that a collection chamber is formed between the end wall, the piston, and the collection bag. An aspirator means is provided for connecting the collection chamber to a source of suction and also to the pool of blood. An outlet means is also provided for connecting the collection chamber to the circulatory system of the patient. The piston is resiliently urged towards the end wall, but is held in place by a locking means while the collection bag is filled. After filling, the locking means is released to allow the piston to move towards the end wall, collapsing the collection bag, and forcing blood back to the circulatory system of the patient. In order to prevent the collapsing collection bag from inadvertently becoming trapped between the side wall of the housing and the piston and preventing operation of the autotransfusion device, a guide means is provided for rotating the piston as the piston moves toward the end wall. In this manner, the collection bag is correspondingly twisted as the collection bag is collapsed so that the collection bag is prevented from being positioned between the side wall and the piston.

In a preferred embodiment of the present invention, the guide means includes a plurality of helical slots which are equidistantly formed along the interior surface of the side wall of the housing. A corresponding plurality of pegs extend laterally from the piston and are located in respective slots. The pegs are constrained to travel in the slots as the piston moves so that the piston is caused to rotate during longitudinal movement. Preferably, there are four of said slots and four of said pegs, and the slots are disposed at approximately a 60° angle.

In the preferred embodiment, the autotransfusion device also includes an automatic air purge unit. The air purge unit is connected to the collection chamber and has a one-way valve which permits air to pass therethrough from the collection chamber, but which blocks the flow of blood therethrough. An auxiliary air purge unit is also provided by using the valved suction outlet of the aspirator means. Should the automatic air purge unit malfunction, the valve on the suction outlet can be opened to allow the air in the collection bag to be withdrawn. In order to retard the fluid flow through the suction outlet, a restriction is placed in the suction outlet. The restriction allows air to pass through fairly quickly, but significantly slows down the flow of blood when blood reaches that point. In this manner, the air is easily purged and the purging is easily stopped when the blood reaches the restriction so that little or no blood is lost.

In order to assure that the collection bag is completely filled, the ratio of heights to diameter of the collection bag is preferably less than 2:1. Advantageously, the ratio of length to diameter is about 1.1:1.

Other features and advantages of the present invention are stated in or apparent from a detailed description of the presently preferred embodiment of the invention described hereinbelow.

BRIEF DESCRIPTION OF THE DRAWINGS

FIG. 1 is a cross-sectional elevation view of an autotransfusion device according to the present invention.

FIG. 2 is a top plan view of the restriction depicted in FIG. 1 in the suction outlet.

DETAILED DESCRIPTION OF THE PREFERRED EMBODIMENT

With reference now to FIG. 1 in which like numerals represent like parts, a cross-sectional view of an autotransfusion device 10 is depicted. The basic autotransfusion device shown is described in detail in pending U.S. application Ser. No. 290,666, entitled "Disposable Autotransfusion Device" now U.S. Pat. No. 4,424,053. This previously filed application is herein incorporated by reference. Autotransfusion device 10 includes a generally cylindrically shaped housing 12 to which an end wall 14 is securely attached. End wall 14 has a reinfusion tube 16 and an auxiliary adapter 18 connected thereto as shown. Ordinarily, auxiliary adapter 18 is suitably closed off and a clamp (not shown) is used to close off reinfusion tube 16.

Spaced opposite end wall 14 and located inside housing 12 is a piston 20. Piston 20 is generally cylindrically shaped and includes four pegs 21 (only one of which is shown) which extend laterally from the side of piston 20 and which are equally spaced around piston 20. Extending upwards from piston 20 and integrally formed therewith are a suction outlet adapter 22 and a suction inlet adapter 24. A suitable tube (not shown) is used to connect suction outlet adapter 22 to a source of suction while another suitable tube (not shown) is used to connect suction inlet adapter 24 to the pool of blood to be collected.

Extending between end wall 14 and piston 20 is a soft vinyl collection bag 26. Collection bag 26 is generally cylindrically shaped and is securely attached to end wall 14 and piston 20 by retaining rings 28 and 30, respectively. In this manner, a collection chamber 32 is formed between end wall 14, piston 20, and collection bag 26.

Attached to the upper portion of housing 12 is a top wall 34. Top wall 34 has an aperture 36 through which suction outlet adapter 22 and suction inlet adapter 24 extend. Top wall 34 includes a circular channel 38 in which one end of a resilient spring 40 is located. The other end of spring 40 is received in a similarly shaped channel 42 in piston 20. Spring 40 urges piston 20 towards end wall 14. However, piston 20 is held in the position shown by a lock ring 44 having tabs 46. By suitably rotating lock ring 44, tabs 46 are indexed to a position in alignment with release slots 48 located around the periphery of piston 20 so that piston 20 is then released to travel toward end wall 14.

Located around the inner periphery of housing 12 are four helical slots 50 (only 3 of which are shown). Helical slots 50 are oriented at approximately a 60° angle to a longitudinal line located along housing 12. Each peg 21 is located in a respective helical slot 50 and pegs 21 are constrained to move in the respective helical slot 50 in which pegs 21 are located.

Located between suction outlet adapter 22 and suction inlet adapter 24 is an automatic air purge unit 52. Air purge unit 52 is the subject of applicant's pending U.S. application entitled "Air Purge Unit For Autotransfusion Apparatus" filed Aug. 14, 1981 now U.S. Pat. No. 4,445,884. This application is herein incorporated by reference. Air purge unit 52 includes a one-way valve 54 which communicates with collection chamber 32 through an outlet 56. Disposed between one-way valve 54 and outlet 56 is a filter element 58. Filter element 58 allows gas to pass therethrough, but is impervious to a liquid such as blood.

Located in suction outlet adapter 22 is a restriction 60. As shown in greater detail in FIG. 2, restriction 60 extends across suction outlet adapter 22 and has a plurality of apertures 62 therein.

In operation, autotransfusion device 10 functions as follows to collect blood from a pool in a patient and to reinfuse the blood into the circulatory system of the patient. Initially, autotransfusion device 10 is in the condition shown in FIG. 1 with auxiliary adapter 18 closed off and reinfusion tube 16 closed by a suitable clamp (not shown). A suitable tube is then attached to suction inlet adapter 24 at one end and at the other end to the pool of blood in the patient. Suction outlet adapter 22 is then connected by a suitable tube to a suitable source of suction. It should be noted that restriction 60 is located in suction outlet adapter 22 at this time. Due to the suction created in collection chamber 32, blood from the patient is drawn through the tube and into collection chamber 32. While restriction 60 does retard the flow of air through suction outlet adapter 22 somewhat, the flow is sufficient to maintain the desired suction in collection chamber 32. During filling of collection chamber 32, it should be noted that one-way valve 54 of air purge unit 52 remains closed.

As suction is applied to collection chamber 32, the ends of collection bag 26 are maintained in that position by end wall 14 and piston 20, respectively. However, the central portion or waist of collection bag 26 is not supported. Therefore, the waist collapses somewhat so that collection bag 26 assumes a "hour glass" configuration. If the waist of collection bag 26 is allowed to form a constriction and divide collection chamber 32 into an upper and lower portion, blood entering suction inlet adapter 24 can pour into the upper portion faster than it is emptied into the lower portion. When this occurs, the upper portion can quickly fill completely and blood can be sucked through suction outlet adapter 22 to the source of suction and be lost for reintransfusion. Besides the loss of blood should the upper portion fill to capacity, the capacity of collection chamber 32 is also sacrificed significantly. Therefore, it is advantageous to prevent the forming of a constriction which prevents the emptying of the upper portion into the lower portion at least as rapidly as the blood is drawn into collection chamber 32. In order to prevent the tight constriction, the height to diameter ratio of collection bag 26 should be less than 2:1. In order to maximize the capacity of collection chamber 32 while minimizing the chances of a tight constriction forming, the ratio of height to diameter of collection bag 26 is preferably 1.1:1.

After collection chamber 32 is filled with blood, or when it is desired to reinfuse the blood collected in collection chamber 32 back into the patient, the tube leading to the suction source is disconnected and clamped and the tube leading to the pool of blood is similarly clamped. At this time, collection chamber 32 usually contains some amount of air. Next, lock ring 44 is rotated so that tabs 46 align with slots 48 in piston 20. When this occurs, spring 40 immediately urges piston 20 towards end wall 14. This creates a pressure inside of collection chamber 32 which is greater than atmosphere. As this occurs, any air trapped in collection chamber 32 is thereby forced through air purge unit 52 and one-way valve 54. It should be noted that outlet 56 is located at the highest point in collection chamber 32 so that all the air in collection chamber 32 is eventually forced out through outlet 56. When all of the air is gone, the blood remaining in collection 32 also travels up outlet 56 to filter element 58. When the blood reaches filter element 58, it is prevented from traveling any further and at this time all of the air has been purged from collection chamber 32.

Should the automatic action of air purge unit 52 malfunction for any reason, it is still important to purge the air from collection chamber 32. In order to accomplish this, suction outlet adapter 22 with restriction 60 in place is used as an auxiliary air purge unit. Thus, by releasing the clamp holding the tube leading to suction outlet adapter 22, air is allowed to pass through suction outlet adapter 22 and restriction 60 to atmosphere. Due to the force of spring 40 on piston 20 and the resultant pressure created in collection chamber 32, the rush of air through suction outlet adapter 22 would be very rapid if not for restriction 60. With restriction 60, the flow of air through suction outlet adapter 22 is reduced. This makes the purging of air from collection chamber 32 through the auxiliary air purge unit much simpler. In addition, restriction 60 presents a significant barrier to flow of blood. Thus, when all of the air is purged from collection chamber 32 and blood is travelling up suction outlet adapter 22, very little blood will pass through restriction 60 before the operator notices that the air has been purged and again clamps the tube leading to suction outlet adapter 22. If not for restriction 60, a significant amount of blood could rush through such an outlet adapter 22 as the air is being purged and be lost.

By way of example, if restriction 60 is located in a $\frac{3}{8}''$ inside diameter suction adapter 22, and if the twelve apertures 62 are 0.032" in diameter, the passage of air would occur at approximately 28 liters per minute. However, the passage of fluid through restriction 60 would be at least five times slower.

When piston 20 is released from lock ring 44, spring 40 immediately causes piston 20 to travel longitudinally towards end wall 14. However, as pegs 21 extending from piston 20 are constrained to move in helical slots 50, any longitudinal movement of piston 20 is also accompanied by a corresponding rotational movement caused by pegs 21 travelling in helical slots 50. For this reason, both tabs 46 and release slots 48 are parallelogram shaped with the longitudinal sides parallel to the longitudinal axes of helical slots 50. This shape allows an easy release of piston 20 by lock ring 44.

After the air is purged from collection chamber 32, reinfusion tube 16 is connected to the circulatory system of the patient and unclamped. The force created by spring 40 then causes collection bag 26 to collapse and the blood in collection chamber 32 to be reinfused into the patient. Due to the pressure created in collection chamber 32, the waist of collection bag 26 tends to be pressed outward to the walls of housing 12. If piston 20 traveled directly toward end wall 14 without rotating, it would be possible for the pressed out portion of collection bag 26 to become wedged between piston 20 and housing 12 as collection bag 26 collapses. This would then prevent piston 20 from travelling any further and the operation of autotransfusion device 10 would be prevented. However, by causing piston 20 to rotate with pegs 21 in helical slots 50, collection bag 26 is similarly twisted as piston 20 travels toward end wall 14. This twisting action on collection bag 26 causes the waist of collection bag 26 to be constricted somewhat toward the central axis of housing 12 and away from the wall of housing 12. This prevents collection bag 26 from becoming wedged between piston 20 and housing 12 and interferring with the proper operation of autotransfusion device 10.

While the present invention has been described with respect to an exemplary embodiment thereof, it will be understood by those of ordinary skill in the art that these and other variations and modifications can be effected within the scope and spirit of the invention.

We claim:

1. An autotransfusion device for collecting blood from a pool in a patient and for subsequently returning the collected blood to the circulatory system of the patient comprising:

a rigid cylindrical housing having an end wall and a side wall;

a movable piston located in said housing;

a generally cylindrical, deformable collection bag located in said housing, the peripheral ends of said collection bag being attached, respectively, adjacent the periphery of said end wall and the periphery of said piston such that a collection chamber is formed between said end wall, said piston and said collection bag;

aspirator means for connecting said collection chamber to a source of suction and to the pool of blood;

outlet means for connecting said collection chamber to the circulatory system of the patient;

resiliency means located in said housing for resiliently urging said piston towards said end wall and collapsing said collection bag;

locking means for releasably locking said piston spaced from said end wall during collection of the blood from the pool such that after said collection bag is adequately filled, said locking means is released to force the collected blood from said collapsing collection bag to the circulatory system of the patient as said piston is urged by said resiliency means toward said end wall; and guide means for rotating said piston about the longitudinal axis of said housing as said piston moves toward said end wall such that said collection bag is correspondingly twisted as said collection bag is collapsed so that said collection bag is prevented from becoming inadvertently trapped between said side wall and said piston.

2. An autotransfusion device as claimed in claim 1 wherein said guide means includes a plurality of helical slots equidistantly formed in the interior surface of said side wall and a corresponding plurality of pegs extending laterally from said piston which are located in respective said slots such that said pegs are constrained to travel in said slots and cause said piston to rotate during longitudinal movement.

3. An autotransfusion device as claimed in claim 2 wherein there are four of said slots and four of said pegs.

4. An autotransfusion device as claimed in claim 3 wherein said slots are disposed approximately at a 60° angle to a longitudinal line on said side wall.

5. An autotransfusion device as claimed in claim 1 and further including an automatic air purge unit connected to said collection chamber having a one-way valve means for permitting air to pass therethrough from said collection chamber to atmosphere while blocking the flow of blood therethrough and wherein said aspirator means includes a valved suction outlet having a restriction to fluid flow therein such that after said collection bag is filled, said valved suction outlet is closed and air is purged from said air purge unit when said piston is urged toward said end wall and during an inadvertent malfunction of said air purge unit said valved suction outlet is opened and air is then purged through said restriction and out of said valved outlet with said restriction offering a significant resistance to flow of the blood to prevent any significant loss of blood after the air is purged.

6. A autotransfusion device as claimed in claim 5 wherein said restriction is an apertured insert located in said suction outlet.

7. An autotransfusion device as claimed in claim 1 wherein said collection bag is made of a soft vinyl plastic and the ratio of length to diameter is less than 2:1.

8. An autotransfusion device as claimed in claim 7 wherein the ratio of length to diameter is about 1.1:1.

9. A transfusion device for delivering blood to the circulatory system of a patient comprising:
 an elongate housing;
 outlet means for connecting said housing to the circulatory system of the patient;
 a longitudinally and laterally deformable blood bag located in said housing and connected to said outlet means;
 a spring biassed collapsing means in said housing coupled to said bag for collapsing said blood bag longitudinally and causing the blood therein to flow through said outlet means; and
 a twisting means coacting with and rotating said collapsing means for twisting and collapsing said blood bag laterally as said blood bag is collapsed longitudinally to prevent said blood bag from interferring with the operation of said collapsing means.

10. A transfusion device as claimed in claim 9 and further including an aspirator means for initially collecting blood from the patient.

11. A transfusion device as claimed in claim 9 wherein said blood bag is cylindrically shaped.

12. A transfusion device as claimed in claim 11 wherein said blood bag is made of a soft vinyl plastic and has a ratio of length to diameter of less than 2:1.

13. A transfusion device as claimed in claim 11, wherein said collapsing means includes a piston which is resiliently urged against said blood bag, collapsing said blood bag.

14. A transfusion device as claimed in claim 13, wherein said blood bag is attached to said piston at one end and to said housing at the other end, and said twisting means includes a means for causing said piston to rotate as said piston is resiliently urged against said blood bag.

* * * * *